United States Patent [19]

Parker et al.

[11] 4,452,672
[45] Jun. 5, 1984

[54] PROCESS AND APPARATUS FOR POLAROGRAPHIC DETERMINATION OF OXYGEN AND CARBON DIOXIDE

[75] Inventors: Dawood Parker; David T. Delpy, both of London, England

[73] Assignee: University College London, London, England

[21] Appl. No.: 455,615

[22] Filed: Jan. 4, 1983

[30] Foreign Application Priority Data

Jan. 7, 1982 [GB] United Kingdom ................ 8200412

[51] Int. Cl.$^3$ ............................................ G01N 27/46
[52] U.S. Cl. .................................. 204/1 T; 204/1 K; 204/1 P; 204/406; 204/407; 204/412; 204/415; 128/635
[58] Field of Search ............... 204/1 K, 1 P, 406, 407, 204/412, 415; 128/635

[56] References Cited

U.S. PATENT DOCUMENTS

| | | | |
|---|---|---|---|
| 3,639,829 | 2/1972 | Harnoncourt | 204/1 P |
| 3,763,422 | 10/1973 | MacPhee et al. | 204/1 P |
| 3,997,420 | 12/1976 | Buzza | 204/406 |
| 4,197,853 | 4/1980 | Parker | 204/415 |
| 4,324,256 | 4/1982 | Vesterager | 204/415 |
| 4,377,446 | 3/1983 | Albery | 204/1 K |

FOREIGN PATENT DOCUMENTS 8102831 10/1981 European Pat. Off. ............ 128/635

Primary Examiner—R. L. Andrews
Assistant Examiner—Terryence Chapman
Attorney, Agent, or Firm—McAulay, Fields, Fisher, Goldstein & Nissen

[57] ABSTRACT

The determination of the concentration of compounds such as $CO_2$ having an influence on the pH of a medium during polarography is described. Characteristics of polarograms when obtained in unbuffered electrolytes (the polarogram plateau slope position of the upper knee and half-wave potential thereof) are pH-sensitive. These can be detected electronically and signals processed to provide a measure of such concentrations.

In one preferred embodiment (FIG. 2) a miniature $pO_2$ polarographic sensor has cathode channels (A) and (B) biased respecitvely at $-750$ mV and $-950$ mV. The output of channel (A) provides $pO_2$ as in normal polarography. The output of (B) is divided (6) and further corrected for $pO_2$ (8,10) to provide $pCO_2$.

The apparatus is especially useful for simultaneous $pO_2$, $pCO_2$ monitoring in physiological fluids without the need for a separate $pCO_2$ sensor.

14 Claims, 6 Drawing Figures

PROCESS AND APPARATUS FOR POLAROGRAPHIC DETERMINATION OF OXYGEN AND CARBON DIOXIDE

FIELD OF THE INVENTION

This invention relates to polarography and in particular to apparatus for the simultaneous polarographic sensing of $pO_2$ and $pCO_2$ in physiological media.

BACKGROUND OF THE INVENTION

Measurement of gas partial pressures in physiological fluids by polarography is well-known. Polarographic sensors are used extensively, for example, in the monitoring of $pO_2$ in blood.

The $pO_2$ sensors are generally based on a design described by L. C. Clark (e.g. see U.S. Pat. No. 2,913,386) and include a noble metal cathode, a buffered electrolyte and a reference anode. The cathode is normally isolated from the medium under investigation by a permeable membrane, but such a membrane is not essential.

A D.C. potential is applied to electrodes. Oxygen present in the electrolyte (having migrated from the medium under investigation through the permeable membrane or through the skin) is electrochemically reduced at the cathode, and the magnitude of current flow is employed as a measure of $pO_2$.

The well-known current versus cathode voltage polarogram for $pO_2$ sensing consists of a curve of increasing current with increasing cathode voltage (to more negative values). The curve has pronounced "knees" at about $-600$ and $-900$ mV (all cathode potentials quoted herein are relative to a silver/silver chloride reference anode) with a near horizontal plateau between these values. For $pO_2$ measurement it is customary to set the cathode polarising voltage on this plateau (typically $-750$ mV) whereby, as $O_2$ is reduced at the cathode, current flow is directly proportional to oxygen concentration.

The sensing of $pCO_2$ in physiological media such as blood is conducted using miniature pH electrodes such as those described by J. W. Severinghaus & A. F. Bradley (1958), J. Appl. Physiol. 13, pp 515–520. Such sensors include a pH electrode (normally a small glass electrode), a reference electrode, and an unbuffered electrolyte. The pH electrode is generally isolated from the medium under investigation by a permeable membrane. Carbon dioxide migrates through the membrane from the medium to dissolve as carbonic acid in the electrolyte. This results in a change in pH which is monitored by the change in EMF between the electrodes. The latter provides a (logarithmic) measurement of $pCO_2$.

Combined sensors for both $pO_2$ and $pCO_2$ measurements have been proposed. One such is described in U.K. Patent Specification No. 2005418 and includes a glass pH electrode for $pCO_2$ sensing, a silver cathode for $pO_2$ sensing, a common silver/silver chloride reference electrode and an unbuffered alkaline electrolyte. The components of the sensor were isolated from the medium to be investigated by a permeable membrane. It was somewhat surprising that the $pO_2$ electrode measurements were unaffected by $pCO_2$ and vice-versa. Despite the advantages of this combined sensor, it does include glass components (the glass pH electrode) and there may be resistance to its use in in vivo sensing—e.g. intravascularly.

We have now devised an apparatus for simultaneous $pO_2$ and $pCO_2$ sensing by polarography and which employs a simple sensor avoiding the use of a separate pH electrode for the $pCO_2$ measurement.

In an unbuffered electrolyte (i.e. one sensitive to pH changes brought about, say, by changes in $pCO_2$ certain characteristics of the above-described $pO_2$ polarogram are pH-sensitive. Not only may these characteristics be employed to measure $pO_2$, but also $pCO_2$. This would not have been possible with early designs of $pO_2$ sensors since the change in pH brought about by the production of hydroxyl ions would itself be significant. However with miniature $pO_2$ sensors now in use, the current flow on $O_2$ reduction is so small (measured in nanoamperes) that the corresponding change in the number of hydroxyl ions does not significantly alter the overall pH even in an unbuffered electrolyte.

Thus, based upon these facts, we have now realised that features of a $pO_2$ polarogram may be employed to measure both $pO_2$ and $pCO_2$, thus avoiding the need for a separate $pCO_2$ sensor.

SUMMARY OF THE INVENTION

In accordance with the invention we provide an apparatus for the determination of the concentration of a component having an influence on the pH of a medium, which comprises a polarographic sensor which, in use, is in contact with said medium, and means for processing the output of the sensor to provide pH-dependent signals and for processing the latter to provide an output which is a measure of said concentration.

We also provide a method of determining the concentration of a component having an influence on the pH of a medium which comprises providing a polarographically-sensed signal representative of said medium, processing said signal to provide a pH-dependent signal and processing the latter to provide an output which is a measure of said concentration.

DESCRIPTION OF THE PREFERRED EMBODIMENTS

Figure 1:
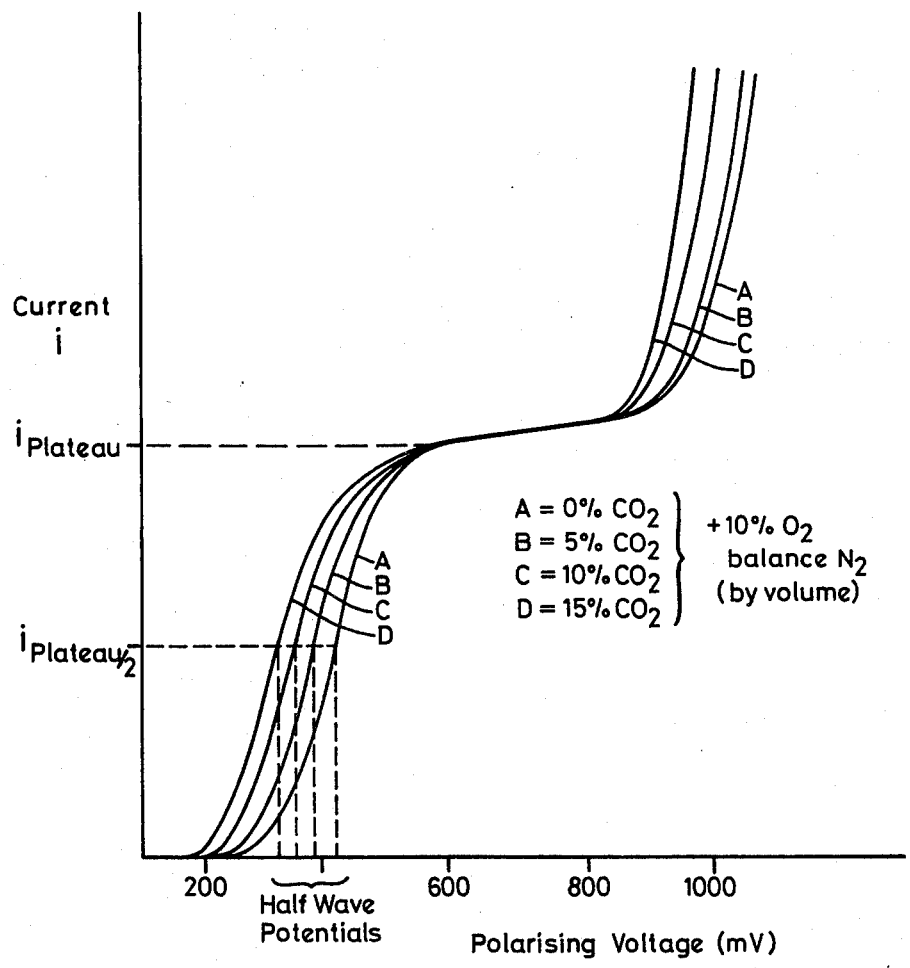
FIG. 1 illustrates four schematic $O_2$ polarograms obtained in the presence of varying concentrations of $CO_2$, as measured by a miniature Clark-type membrane-covered polarographic sensor, and which will be employed to explain the present invention.

Referring to FIG. 1, the four polarograms are shown with the characteristic knees at about $-600$ and $-900$ mV with a near horizontal plateau therebetween. The absolute values of the current flowing have been normalised at a polarising voltage of $-750$ mV. Various characteristics of the curve are pH dependent, and these (either alone or in combination) may be employed to give a measure of $pCO_2$ without the need for a separate pH electrode. We have found that the exact position of both upper and lower knees, the slope of the plateau, and the half-wave potential can all be employed to determine $pCO_2$. Of these, we have so far found that the half-wave potential provides the most convenient measurement (it is less subject to variations in $pO_2$) and the embodiment described later in relation to FIGS. 5 and 6 relates to this. In FIG. 1, the change of plateau slope with $pCO_2$ has been omitted for clarity: in fact the slope increases slightly with increasing $pCO_2$.

Figure 2:
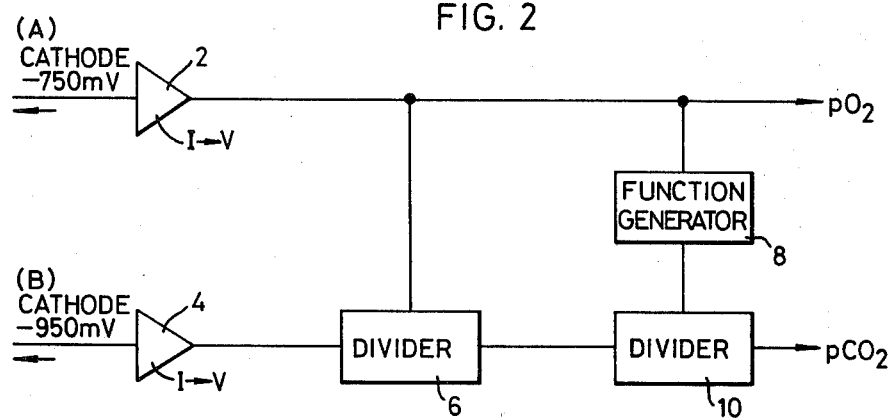
FIGS. 2, 3 and 4 illustrate respectively block electronic diagrams of circuits for processing the signals from a $pO_2$ polarographic sensor so as to obtain $pCO_2$ and $pO_2$ results, in accordance with three preferred embodiments of the invention.

Referring to FIG. 2, a circuit is shown for use with a standard miniature $pO_2$ polarographic sensor with an unbuffered electrolyte. Measurements are made at polarising voltages of $-750$ and $-950$ mV. Very roughly:

$$i_{750} = f(pO_2)$$

$$i_{950} = f(pO_2) \cdot f(pCO_2)$$

where $i_{750}$, $i_{950}$ are the respective currents at $-750$, $-950$ mV.
Therefore $$(i_{950}/i_{750}) \approx f(pCO_2).$$

Either a single cathode successively switched between these two voltages may be employed, or a pair of cathodes, one at each voltage. In FIG. 2, two separate cathodes have been shown.

In either case, the cathode signals at these two voltages are processed in separate channels (A) and (B), each initially being fed to current-to-voltage converters 2 and 4 respectively. The output of converter 2 provides a representation of $pO_2$ as in normal polarography, whereas the output of converter 4 is divided by the $pO_2$ signal from converter 2 in divider 6. To a rough approximation this gives a measure of $pCO_2$, but for more accurate next order results this signal may be further divided by a function of the $pO_2$ signal with a function generator 8 and divider 10. The output of the latter provides the next order $pCO_2$ result (for a description of this next order correction, see later).

Figure 3:
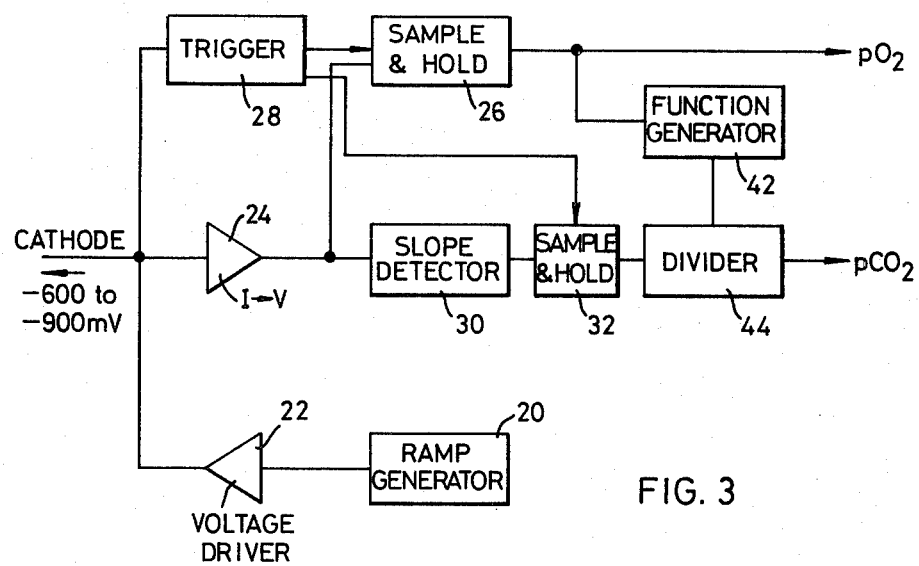

Referring to FIG. 3, a circuit is again shown for use with a standard miniature $pO_2$ polarographic sensor with an unbuffered electrolyte. In this instance the slope of the plateau is directly measured to provide the $pCO_2$ result.

A ramp generator 20 provides a sawtooth output to actuate a voltage driver 22 which provides a sawtooth cathode bias between $-600$ and $-900$ mV. The cathode output is supplied to a current-to-voltage converter 24 which supplies a sample-and-hold circuit 26 triggered from a Schmidt trigger 28 actuated at the midpoint of the cathode ramp voltage ($-750$ mV). The output of the sample-and-hold circuit 26 (proportional to the current flow at $-750$ mV) provides a measure of $pO_2$. The output of current-to-voltage converter 24 is additionally applied to a slope detector (a differentiator) 30, the output of which at $-750$ mV approximates to $pCO_2$. This output is supplied to a sample-and-hold circuit 32 which is also triggered at $-750$ mV. The circuit 32 output provides the $pCO_2$ measurement. As with the FIG. 2 circuit, a more accurate next order approximation is obtained by correcting the output of the slope detector as a function of $pO_2$. This is obtained by generating a function of $pO_2$ with function generator 42 and dividing the signals in divider 44. The output of the latter provides the $pCO_2$ measurement.

Figure 4:
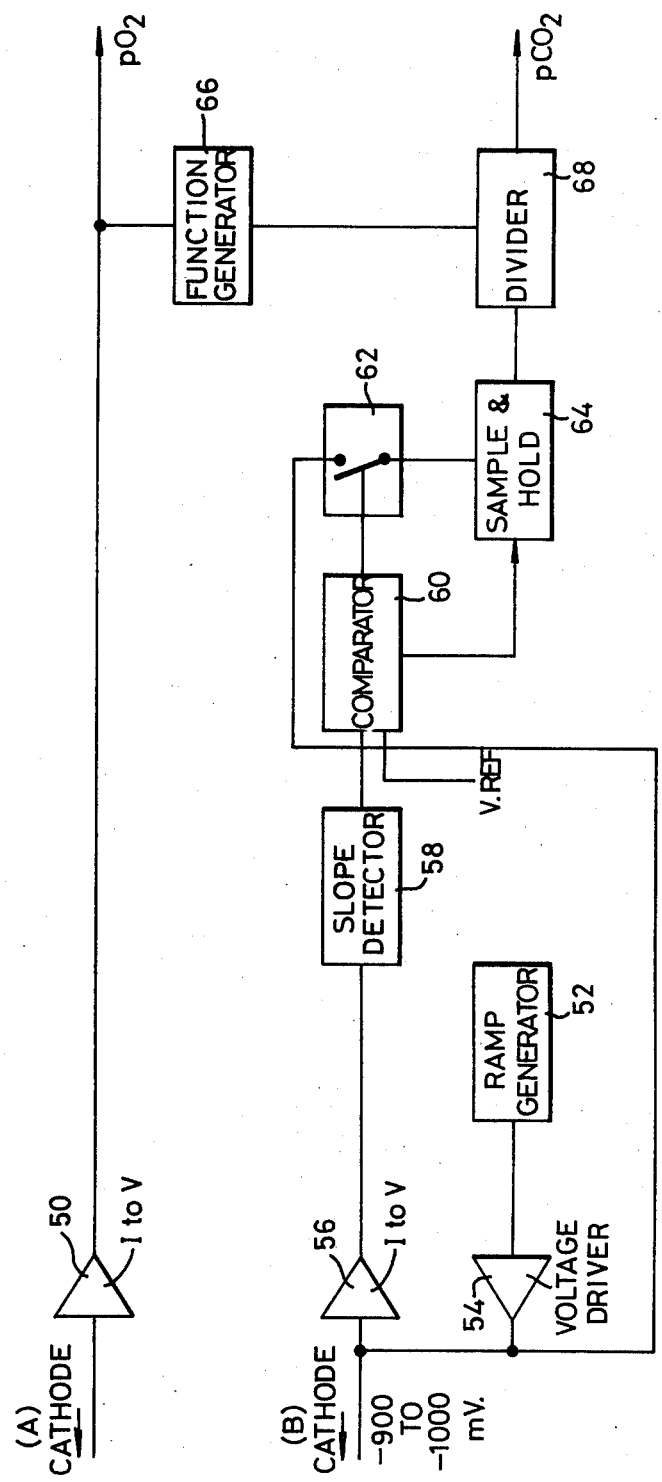

Referring to FIG. 4, a circuit is once more shown for use with a standard miniature $pO_2$ polarographic sensor with an unbuffered electrolyte. In this embodiment the position of the upper knee ($pCO_2$-sensitive) is detected by determining the rate of change of current as the cathode is scanned over a voltage range near the top of the plateau: e.g. $-900$ to $-1000$ mV. Either a single cathode may be employed, first at $-750$ mV to give the $pO_2$ result and secondly scanned over $-900$ to $-1000$ mV, or separate cathodes may be employed for these functions.

As in the FIG. 2 embodiment these signals are processed in separate channels (A) and (B). The $-750$ mV cathode signal is supplied to a current-to-voltage converter 50, the output of which provides $pO_2$. A ramp generator 52 actuates a voltage driver 54 to provide, to the second channel (B), a sawtooth cathode bias between $-900$ and $-1000$ mV. The second channel signal is supplied to a current-to-voltage converter 56, and the latter drives a slope detector 58. The output of the slope detector 58 is compared to a reference voltage in comparator 60, the reference voltage being selected such that the comparator detects the rapid change in slope at the knee. The comparator output, when valid, closes analog switch 62, which supplies the output of the driver 54 to a sample-and-hold circuit 64 triggered by the comparator output. To a first approximation the result is a measure of $pCO_2$ and a more accurate result is obtained by correcting for $pO_2$ by means of function generator 66 and divider 68.

The correction of the rough $pCO_2$ measurement in these embodiments for $pO_2$ may, to a first approximation, be made by creating, in function generators 8, 42, and 66, a linear function of $pO_2$. However, in practice, it will be possible by calibration to provide more accurate results by applying a more complex, non-linear function of $pO_2$.

Figure 5:
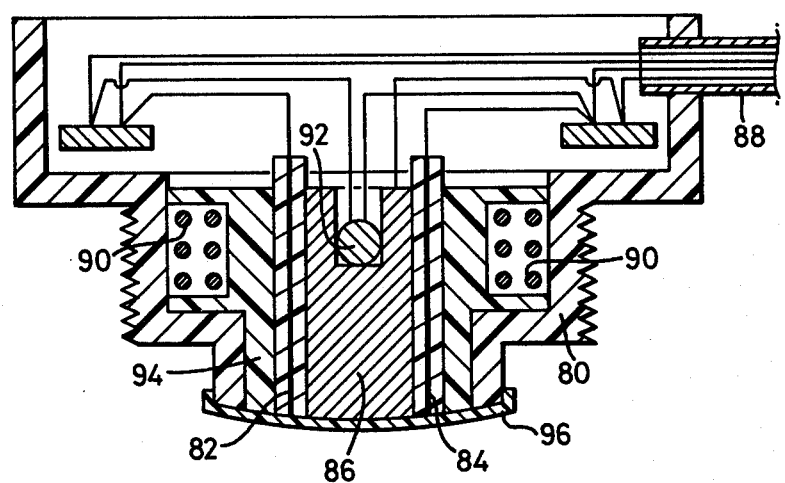
FIG. 5 is a schematic cross-section through a dual cathode transcutaneous sensor for use in a further embodiment of the invention.
Figure 6:
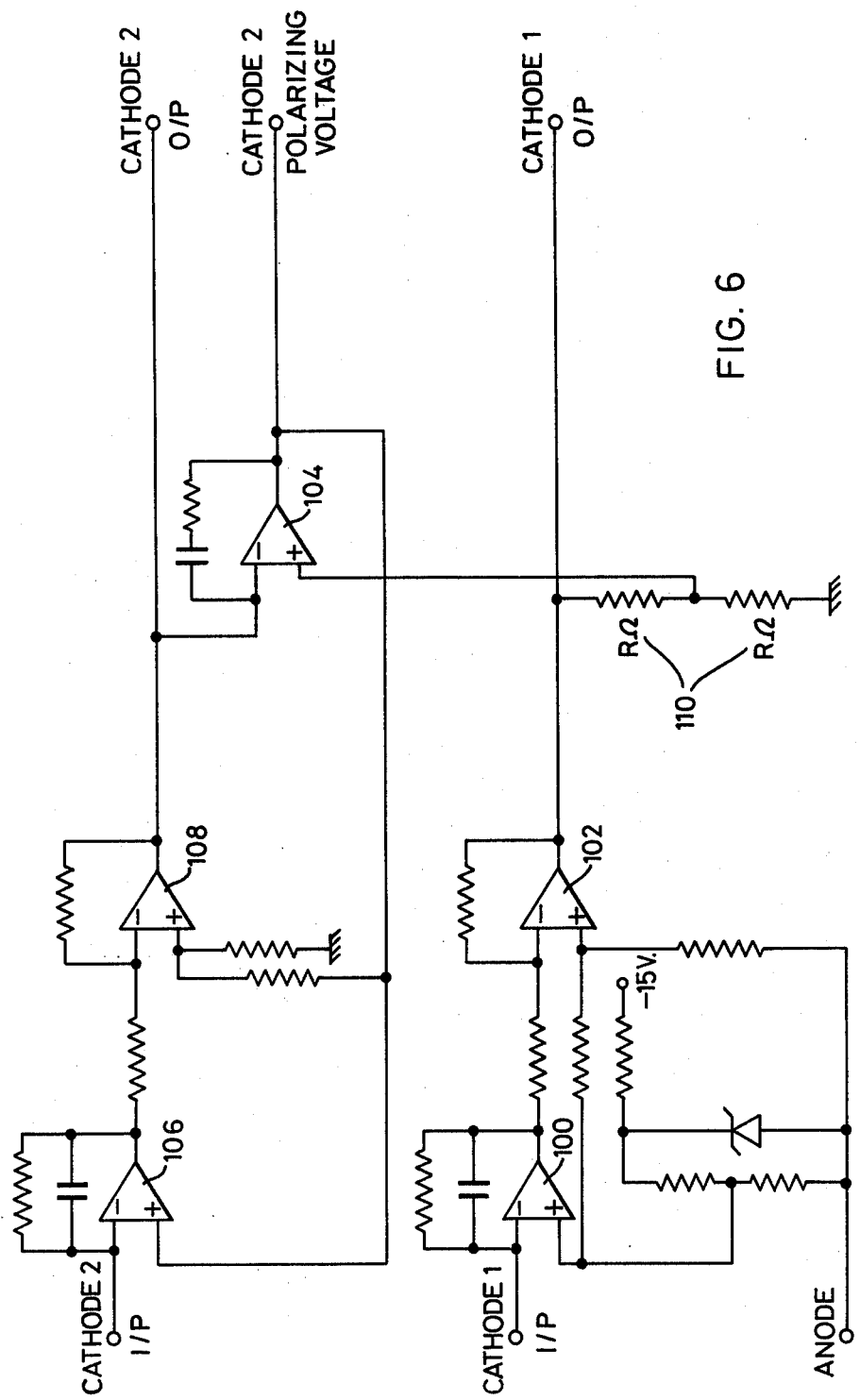
FIG. 6 is a diagram of the electric circuit employed to obtain $pO_2$ and $pCO_2$ measurements from the sensor of FIG. 5.

The embodiment shown in FIGS. 5 and 6 is designed to detect the half-wave potential for $pO_2$ in the presence of $CO_2$. The half-wave potential, as is well-known, is the potential which will provide half the plateau current. It is the point of inflection for the polarogram before it reaches the lower knee of the curve. It is normally used in polarography for identifying the ionic species being electrochemically discharged. We have found that the half-wave potential is proportional to $pCO_2$ and is relatively insensitive to changes in $pO_2$.

A dual cathode transcutaneous sensor for use in such half-wave potential detection is shown in FIG. 5. One cathode is connected to circuitry (FIG. 6) to determine the plateau current (and hence gave a measure of $pO_2$) whereas the other cathode applies half the thus-measured cathode current and hence supplies the half-wave potential. The latter is proportional to $pCO_2$.

Referring to FIG. 5, the sensor comprises a housing 80 containing a pair of polarographic cathodes 82, 84 and a central anode 86 electrically connected via a terminal board to a connector cable 88. The latter leads to the electrical circuit of FIG. 6. A heater 90 is lodged within housing 80 and temperature control is provided by means of a thermistor 92 as is known. The electrodes, thermistor and heater are potted in an epoxy resin 94. A permeable membrane 96 covers the electrodes. The electrodes may be of standard materials, typically platinum.

Referring to FIG. 6, one cathode is polarised at a voltage of $-750$ mV to ensure that the cathode is held on the plateau and the cathode current is proportional to $pO_2$. The input from this cathode is supplied to a current-to-voltage converter 100 and thence to operational amplifier 102. The output of the latter is taken as the $pO_2$ measurement but is also supplied as one input to comparator 104, (after division by two by means of resistor chain 110).

The input from the second cathode passes through current-to-voltage converter 106, operational amplifier 108, and is supplied as the second input to comparator 104. The output of the latter is taken as a feedback line 112 to a second input of current-to-voltage converter 106 and is also employed as the polarising voltage for the second cathode.

This arrangement ensures that the second cathode is supplied with the appropriate voltage to maintain the cathode at the current equal to half the plateau current. The output from the amplifier 108 is therefore also taken as the $pCO_2$ measurement from the system.

Although much of the above-described signal processing may be accomplished by hard-wired logic circuits, it may be desirable to generate the $pO_2$ and $pCO_2$ results by signal processing with a microprocessor. The latter would enable the cathode signals to be processed with a high degree of precision.

Although the invention thus far has been described in the context of the influence of $pCO_2$ on $O_2$ polarograms because, for many physiological conditions, it is desirable to monitor both $pO_2$ and $pCO_2$, the invention has much wider implications.

For example, if it is not desired to sense $pO_2$ whilst monitoring $pCO_2$, then it is not essential to monitor the influence of $CO_2$ on an $O_2$ polarogram—it might be more desirable to select a different electrochemically-reducible medium and electrolyte system upon which $pCO_2$ has a more marked and measureable effect.

Furthermore, since the invention measures $pCO_2$ as a consequence of pH influence on polarograms, it could possibly be employed to measure concentrations of pH-influencing components other than $CO_2$, for example $SO_2$ or $NH_3$.

Although in the above-described embodiments it has been assumed that the hydroxyl ion production is insufficient to upset the pH measurements, if desired their effect may be reduced by employment of the technique described by J. W. Severinghaus, J. Appl. Physiol. 51, pp 1027, 1032. This involves the use of a counter electrode (e.g. of anodised aluminium or platinum) which generates sufficient hydrogen ions to balance stoichiometrically the production of hydroxyl ions. The influence of the latter on the system is thus negated.

We claim:

1. The method of determining the partial pressure in a medium of a first gas and of a second gas, wherein said second gas in aqueous solution generates an acid or a base comprising the steps of:
   providing a polarographically sensed first signal at a first bias voltage, said first signal being representative of the concentration of said first gas,
   providing a polarographically sensed second signal at at least a second bias voltage, said second signal being representative of the concentration of both of said gases, and
   comparing said first signal and said second signal to provide a third signal representative of the concentration of said second gas.

2. A polarographic sensor for use in the determination of the concentration of a component having an influence of the pH of a medium, which comprises:
   a pair of substantially identical cathodes each of which is independently operable to detect the current and voltage relationship of two different positions on the polarograph characteristic of said cathodes,
   biasing means to bias said cathodes to at least first and second voltages respectfully, and
   circuit means coupled to the outputs of said sensor to provide a measurement of said component having an influence on the pH of a medium.

3. An electrode device for measuring the partial pressure in a medium of a first gas and of a second gas, wherein said second gas in aqueous solution generates an acid or a base, comprising:
   a polarographic sensor adapted to be placed in contact with the medium having said first and second gases as components thereof, said sensor having a first working electrode,
   variable biasing means to bias said working electrode to at least first and second bias voltages,
   first circuit means coupled to the output of said sensor at said first bias voltage to provide a first measurement signal representative of the concentration of said first gas,
   second circuit means coupled to the output of said polarographic sensor at at least said second bias voltage to provide a second measurement signal representative of the concentration of both of said gases, and
   third circuit means coupled to said first measurement signal and to said second measurement signal to provide a third measurement signal representative of the concentration of said second gas.

4. The electrode device of claim 3 wherein said first gas is oxygen.

5. The electrode device of claims 3 or 4 wherein said second gas is carbon dioxide.

6. The electrode device of claims 3 or 4 wherein said polarographic sensor includes solely unbuffered electrolyte.

7. The electrode device of claims 3 or 4 wherein said third circuit means includes means for dividing said second measurement signal by said first measurement signal.

8. The electrode device of claims 3 or 4 wherein said third circuit means includes means for determining the slope of the characteristic curve of said polarographic sensor at said first bias voltage.

9. The electrode device of claims 3 or 4 wherein said second bias voltage is the half-wave potential of the polarogram of said sensor.

10. The electrode device of claims 3 or 4 wherein said second bias voltage is at a point beyond the upper knee of the polarogram of said sensor.

11. The electrode device of claims 3 or 4 where said variable biasing means provide a range of bias voltages.

12. An electrode device for measuring the partial pressure in a medium of a first gas and of a second gas, wherein said second gas in aqueous solution generates an acid or a base, comprising:
   a polarographic sensor adapted to be placed in contact with the medium having said first and second gases as components thereof,
   said sensor having first and second substantially identical working electrodes,
   biasing means to bias said first electrode to a first voltage and said second electrode to at least a second voltage, first circuit means coupled to the output of said first electrode to provide a first measurement signal representative of the concentration of said first gas, second circuit means coupled to the output of said second electrode to provide a second measurement signal representative of the concentration of both of said gases, and third circuit means coupled to said first measurement signal and to said second measurement signal to provide a third measurement signal representative of the concentration of said second gas.

13. The electrode device of claim 12 wherein said first gas is oxygen and said second gas is carbon dioxide.

14. The electrode device of claims 12 or 13 wherein said polarographic sensor includes solely unbuffered electrolyte.

* * * * *